(12) United States Patent
Cabell

(10) Patent No.: US 7,579,062 B2
(45) Date of Patent: Aug. 25, 2009

(54) HYDROXYL POLYMER WEB STRUCTURES COMPRISING A TUFT

(75) Inventor: David William Cabell, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 257 days.

(21) Appl. No.: 11/129,877

(22) Filed: May 16, 2005

(65) Prior Publication Data

US 2005/0281978 A1    Dec. 22, 2005

Related U.S. Application Data

(60) Provisional application No. 60/581,648, filed on Jun. 21, 2004.

(51) Int. Cl.
   *B32B 3/02*    (2006.01)
   *B32B 3/10*    (2006.01)
   *B32B 5/26*    (2006.01)

(52) U.S. Cl. ............... 428/97; 428/92; 428/132; 428/133; 428/134; 428/136; 442/381; 442/389; 442/391; 442/414

(58) Field of Classification Search .......... 428/92, 428/97, 132–134, 136, 174, 175, 179, 180
See application file for complete search history.

(56) References Cited

U.S. PATENT DOCUMENTS

| | | | |
|---|---|---|---|
| 3,062,379 A * | 11/1962 | Bryan | ............ 210/499 |
| 3,511,740 A | 5/1970 | Sanders | |
| 3,684,284 A | 8/1972 | Tranfield | |
| 3,695,270 A | 10/1972 | Dostal | |
| 4,042,453 A | 8/1977 | Conway | |
| 4,379,799 A | 4/1983 | Holmes | |
| 4,465,726 A | 8/1984 | Holmes | |
| 5,062,418 A | 11/1991 | Dyer | |
| 5,180,620 A * | 1/1993 | Mende | ............ 428/138 |
| 5,382,245 A | 1/1995 | Thompson | |
| 5,508,080 A | 4/1996 | Sorimachi et al. | |
| 5,518,801 A | 5/1996 | Chappell | |
| 5,536,555 A | 7/1996 | Zelazoski | |
| 5,554,145 A | 9/1996 | Roe | |
| 5,558,655 A | 9/1996 | Jezzi | |
| 5,628,097 A | 5/1997 | Benson | |
| 5,650,214 A | 7/1997 | Anderson et al. | |
| 5,658,639 A | 8/1997 | Curro | |

(Continued)

FOREIGN PATENT DOCUMENTS

EP    0 963 747 A1    12/1999

(Continued)

OTHER PUBLICATIONS

"Vinylon" Defintion, Polymer Science Dictionary: 2nd Edition. Cahpman & Hall. London. 1997. p. 604.*

(Continued)

*Primary Examiner*—Jenna-Leigh Johnson
(74) *Attorney, Agent, or Firm*—C. Brant Cook

(57) ABSTRACT

Web structures comprising a tuft and methods for making same are provided. More particularly, web structures comprising a polymeric structure comprising a crosslinked, hydroxyl polymer, wherein the web structure comprises a tuft and processes for making such web structures are provided.

21 Claims, 9 Drawing Sheets

U.S. PATENT DOCUMENTS

| | | | |
|---|---|---|---|
| 5,700,255 A | 12/1997 | Curro et al. | |
| 5,725,705 A * | 3/1998 | Nagahama et al. | 156/148 |
| 5,730,738 A | 3/1998 | McFall et al. | |
| 5,792,404 A | 8/1998 | Cree et al. | |
| 5,830,555 A | 11/1998 | Srinivasan | |
| 5,876,391 A | 3/1999 | Roe et al. | |
| 5,916,661 A | 6/1999 | Benson | |
| 5,919,177 A | 7/1999 | Georger | |
| 5,932,316 A | 8/1999 | Cree et al. | |
| 5,968,029 A | 10/1999 | Chappell | |
| 5,989,688 A | 11/1999 | Barge | |
| 5,993,432 A | 11/1999 | Lodge | |
| 6,049,024 A | 4/2000 | Thomas | |
| 6,057,023 A * | 5/2000 | Shimono et al. | 428/92 |
| 6,120,718 A | 9/2000 | Kotek et al. | |
| 6,150,002 A | 11/2000 | Varona | |
| 6,222,092 B1 * | 4/2001 | Hansen et al. | 604/378 |
| 6,350,332 B1 | 2/2002 | Thomas | |
| 6,458,447 B1 | 10/2002 | Cabell | |
| 6,491,928 B1 | 12/2002 | Smith, III | |
| 6,610,391 B2 | 8/2003 | Molee | |
| 6,613,028 B1 | 9/2003 | Daley | |
| 6,647,549 B2 | 11/2003 | McDevitt et al. | |
| 6,716,498 B2 | 4/2004 | Curro et al. | |
| 6,721,987 B2 | 4/2004 | McDevitt et al. | |
| 6,723,160 B2 * | 4/2004 | Mackey et al. | 106/206.1 |
| 6,730,622 B2 | 5/2004 | Curro et al. | |
| 6,740,792 B2 | 5/2004 | Waldroup et al. | |
| D494,369 S | 8/2004 | McDevitt et al. | |
| 6,808,791 B2 | 10/2004 | Curro et al. | |
| 6,830,800 B2 | 12/2004 | Curro et al. | |
| 6,855,220 B2 | 2/2005 | Wildeman | |
| 6,863,960 B2 | 3/2005 | Curro et al. | |
| 6,869,660 B2 | 3/2005 | Wildeman | |
| 7,172,801 B2 * | 2/2007 | Hoying et al. | 428/92 |
| 7,410,683 B2 * | 8/2008 | Curro et al. | 428/133 |
| 2003/0050589 A1 | 3/2003 | McDevitt et al. | |
| 2003/0077970 A1 | 4/2003 | DeLucia | |
| 2003/0097113 A1 | 5/2003 | Molee | |
| 2004/0131820 A1 | 7/2004 | Turner | |
| 2004/0157036 A1 | 8/2004 | Provost et al. | |
| 2004/0161991 A1 | 8/2004 | Walton et al. | |
| 2004/0229008 A1 | 11/2004 | Hoying | |
| 2004/0242097 A1 * | 12/2004 | Hasenoehrl et al. | 442/59 |
| 2004/0265533 A1 | 12/2004 | Hoying | |
| 2004/0265534 A1 | 12/2004 | Curro | |
| 2005/0071938 A1 | 4/2005 | McDevitt et al. | |
| 2005/0118389 A1 | 6/2005 | Wildeman | |

FOREIGN PATENT DOCUMENTS

| | | |
|---|---|---|
| EP | 1132512 A1 * | 9/2001 |
| EP | 1 217 106 B1 | 6/2002 |
| GB | 950 074 | 2/1964 |
| WO | WO 93/01780 | 2/1993 |
| WO | WO 95/15138 A1 | 6/1995 |
| WO | WO 97/00656 A1 | 1/1997 |
| WO | WO 02/100632 A1 | 12/2002 |

OTHER PUBLICATIONS

PCT International Search Report mailed Nov. 14, 2005.

* cited by examiner

HYDROXYL POLYMER WEB STRUCTURES COMPRISING A TUFT

CROSS REFERENCE TO RELATED APPLICATIONS

This application claims priority to U.S. Provisional Application Ser. No. 60/581,648 filed Jun. 21, 2004.

FIELD OF THE INVENTION

The present invention relates to web structures comprising a tuft, more particularly hydroxyl polymer web structures comprising a tuft and methods for making same. Even more particularly, the present invention relates to web structures comprising a tuft wherein the web structures comprise a polymeric structure comprising a crosslinked, hydroxyl polymer and processes for making such web structures.

BACKGROUND OF THE INVENTION

Web structures that comprise polymeric structures, such as fibers and/or films, comprising crosslinked, hydroxyl polymers are known in the art. However, web structures that comprise polymeric structures, such as fibers and/or films, comprising crosslinked, hydroxyl polymers wherein the web structures comprise a tuft are not known in the art.

Accordingly, there is a need for a web structure comprising a polymeric structure, such as a fiber and/or a film, comprising a crosslinked, hydroxyl polymer wherein the web structure comprises a tuft and processes for making such web structures.

SUMMARY OF THE INVENTION

The present invention fulfills the needs described above by providing web structures comprising a polymeric structure, such as a fiber and/or a film, comprising a crosslinked, hydroxyl polymer wherein the web structures comprise a tuft and processes for making such web structures.

In one example of the present invention, a web structure comprising a tuft, wherein the web structure comprises a polymeric structure comprising a crosslinked, hydroxyl polymer, is provided.

In another example of the present invention, a single-ply fibrous structure and/or web structure comprising at least two chemically different compositions, at least one of which is a crosslinked, hydroxyl polymer, wherein the fibrous structure and/or web structure comprises a tuft formed by less than all of the chemically different compositions, is provided.

In even another example of the present invention, a layered web product comprising a ply comprising at least two layers, wherein one of the at least two layers comprises a crosslinked, hydroxyl polymer, wherein one of the at least two layers protrudes through another of the at least two layers forming a tuft, is provided.

In yet another aspect of the present invention, a web product comprising a web structure and/or a layered web structure in accordance with the present invention, is provided.

In even another aspect of the present invention, a process for making a web structure, the process comprising the steps of:

a) providing a polymer melt composition comprising a hydroxyl polymer and a crosslinking system;

b) polymer processing the polymer melt composition to form a polymeric structure;

c) incorporating the polymeric structure into a web structure; and d) subjecting the web structure to a tuft generating process such that a web structure comprising a tuft is produced, is provided.

In still yet another aspect of the present invention, a process for making a web structure, the process comprising the steps of:

a) providing a web structure comprising a polymeric structure comprising a crosslinked, hydroxyl polymer; and b) subjecting the web structure to a tuft generating process such that a tuft is produced in the web structure, is provided.

Accordingly, the present invention provides: a web structure comprising a tuft, wherein the web structure comprises a crosslinked, hydroxyl polymer; a web product comprising such a web structure and processes for making such a web structure.

DETAILED DESCRIPTION OF THE INVENTION

Definitions

Figure 1A:
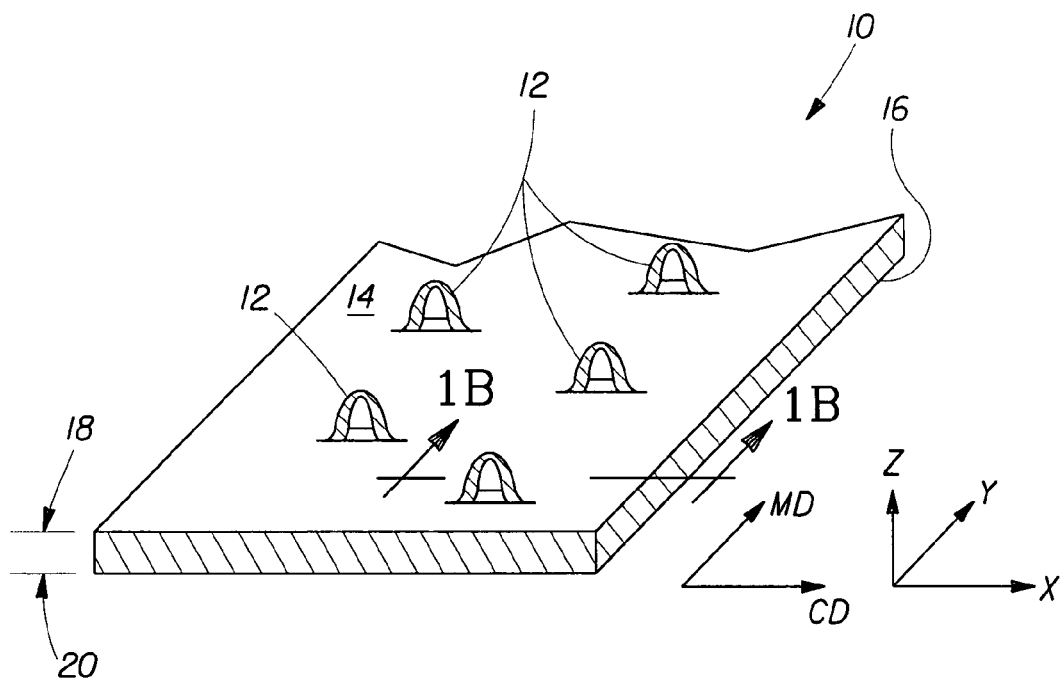
FIG. 1A is a schematic representation of a web structure of the present invention.

"Web Structure" as used herein means a generally planar, physical structure. In one example, a web structure of the present invention comprises a film. In another example, the web structure of the present invention comprises a fibrous structure. In a third example, the web structure of the present invention may comprise both a film and at least one fiber and/or a fibrous structure.

In one example of a web structure according to the present invention, the web structure may be a co-formed web structure comprising a polymeric structure comprising a crosslinked, hydroxyl polymer and another fiber comprising a chemically different composition relative to the polymeric structure.

"Fibrous structure" as used herein means a physical structure that comprises at least one fiber.

"Web product" and/or "sanitary tissue product" as used herein includes but is not limited to a wiping implement for post-urinary and post-bowel movement cleaning (toilet tissue), for otorhinolaryngological discharges (facial tissue), and multi-functional absorbent and cleaning uses (absorbent towels).

"Polymeric structure" as used herein means any physical structure produced by polymer processing a polymer melt composition of the present invention. Nonlimiting examples of such polymeric structures include fibers, films and foams. Such polymeric structures, especially when in fiber form, may be used, optionally along with other physical structures such as cellulosic fibers and thermoplastic water-insoluble polymer fibers, to form web structures. In one example, the polymeric structure of the present invention or at least a portion thereof exhibits no melting point or in other words the polymeric structure is a crosslinked, hydroxyl polymer. In another example, the polymeric structure of the present invention is substantially homogeneous.

The polymeric structure fibers of the present invention may be continuous or substantially continuous. A fiber is continuous if it extends 100% of the MD length of the web structure and/or web product made therefrom. In one example, a fiber is substantially continuous if it extends greater than about 30% and/or greater than about 50% and/or greater than about 70% of the MD length of the web structure and/or web product made therefrom. In another example, a fiber is an elongate, physical structure and/or filament having an apparent length greatly exceeding its apparent width, i.e. a length to diameter ratio of at least about 10.

The polymeric structure fibers may have a fiber diameter as determined by the Fiber Diameter Test Method described herein of less than about 50 microns and/or less than about 20 microns and/or less than about 10 microns and/or less than about 8 microns and/or less than about 6 microns.

The polymeric structures of the present invention, especially fibers of the present invention, may be produced by crosslinking a hydroxyl polymer together. In one example, the polymeric structure, especially in fiber form, formed as a result of the crosslinking, as a whole, exhibits no melting point. In other words, it degrades before melting. Nonlimiting examples of a suitable crosslinking system for achieving crosslinking comprises a crosslinking agent and optionally a crosslinking facilitator, wherein the hydroxyl polymer is crosslinked by the crosslinking agent.

The polymeric structure fibers of the present invention may include melt spun fibers, dry spun fibers and/or spunbond fibers, staple fibers, hollow fibers, shaped fibers, such as multi-lobal fibers and multicomponent fibers, especially bicomponent fibers. The multicomponent fibers, especially bicomponent fibers, may be in a side-by-side, sheath-core, segmented pie, ribbon, islands-in-the-sea configuration, or any combination thereof. The sheath may be continuous or non-continuous around the core. The ratio of the weight of the sheath to the core can be from about 5:95 to about 95:5. The fibers of the present invention may have different geometries that include round, elliptical, star shaped, rectangular, and other various eccentricities.

In another example, the polymeric structure fibers of the present invention may include a multiconstituent fiber, such as a multicomponent fiber. A multicomponent fiber, as used herein, means a fiber having more than one separate part in spatial relationship to one another. Multicomponent fibers include bicomponent fibers, which are defined as fibers having two separate parts in a spatial relationship to one another. The different components of multicomponent fibers can be arranged in substantially distinct regions across the cross-section of the fiber and extend continuously along the length of the fiber.

A nonlimiting example of such a multicomponent fiber, specifically a bicomponent fiber, is a bicomponent fiber in which the crosslinked, hydroxyl polymer represents the core of the fiber and the thermoplastic polymer represents the sheath, which surrounds or substantially surrounds the core of the fiber. The polymer melt composition from which such a fiber is derived may include the hydroxyl polymer and the thermoplastic, water-insoluble polymer.

In another multicomponent, especially bicomponent, fiber example, the sheath may comprise a crosslinked, hydroxyl polymer and the core may comprise a crosslinked, hydroxyl polymer. With respect to the sheath and core, the hydroxyl polymer may be the same or different. Further, the level of hydroxyl polymer may be the same or different.

One or more substantially continuous or continuous fibers of the present invention may be incorporated into a web structure, such as a web. Such a web structure may ultimately be incorporated into a commercial product, such as a single- or multi-ply web product.

In addition to the polymeric structure comprising a crosslinked, hydroxyl polymer, the web structures of the present invention may comprise other structures such as fibers and/or other polymers such as thermoplastic polymers. "Fiber" as used herein means an elongate physical structure and/or filament having an apparent length greatly exceeding its apparent width, i.e. a length to diameter ratio of at least about 10. More specifically, as used herein, "fiber" refers to web-making fibers.

"Hydroxyl polymer" as used herein means any material that requires a softener or solvent to be present in order to be sufficiently softened into a flowable state, which permits shaping of the hydroxyl polymer. When such hydroxyl polymers are crosslinked, the crosslinked, hydroxyl polymer decomposes before melting. In other words, the crosslinked, hydroxyl polymer exhibits no melting point.

"Polymer" as used herein generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

"Tufted region" as used herein means a region of the fibrous structure and/or fibrous product that comprises one or more tufts. A "tuft" as used herein means a region of the fibrous structure and/or fibrous product that is extended from the fibrous structure and/or fibrous product along the z-axis ("z-axis" as used herein is commonly understood in the art to indicate an "out-of-plane" direction generally orthogonal to the x-y plane as shown in FIG. 1, for example). In one example, a tuft is a continuous loop that extends along the z-axis from the fibrous structure and/or fibrous product. The tuft may define an interior open or substantially open void area that is generally free of fibers. In other words, the tufts of the present invention may exhibit a "tunnel-like" structure, instead of a "tent-like" rib-like element that exhibits continuous side walls as is taught in the prior art. In one example, the tunnel is oriented in the MD of the fibrous structure and/or fibrous product. In another example, as a result of the tuft, a discontinuity is formed in the fibrous structure and/or fibrous product in its x-y plane. A "discontinuity" as used herein is an interruption along the side/surface of the fibrous structure and/or fibrous product opposite the tuft. In other words, a discontinuity is a hole and/or recess and/or void on a side/surface of the fibrous structure and/or fibrous product that is created as a result of the formation of the tuft on the opposite side/surface of the fibrous structure and/or fibrous product. In one example, a deformation in a surface of fibrous structure and/or fibrous product such as a bulge, bump, loop or other protruding structure that extends from a surface of the fibrous structure and/or fibrous product of the present invention.

In one example, the chemically different composition that forms the tuft may be hydrophilic relative to the chemically different composition that is not part of the tuft.

In one example, the tufts of the fibrous structure and/or fibrous product of the present invention may be increase the caliper of the fibrous structure and/or fibrous product by at least about 10% and/or at least about 20% relative to the fibrous structure and/or fibrous product prior to formation of the tufts.

In another example, the tufts may be oriented inward in a multi-ply fibrous product, they may be oriented outward on a multi-ply fibrous product, and they may be oriented such that one ply has the tufts oriented inward and another ply has the tufts oriented outward in/on the multi-ply fibrous product.

In yet another example, the tufted fibrous structure and/or fibrous product of the present invention may be convolutedly wound to form a roll of the fibrous structure and/or fibrous product. Such a roll may exhibit an effective caliper that is greater than the combined caliper of the untufted fibrous structure and/or fibrous product.

In still another example, the tufts of the fibrous structure and/or fibrous product may be phased to embossing, printing and/or perforations on and/or within the fibrous structure and/or fibrous product.

In yet another example, the tufts of the fibrous structure and/or fibrous product may generate enhanced aesthetics through creating differential height/elevation and/or differential texture regions, differential opacity regions, differential color (when tufts have colors (same or varied)), phasing with ink or emboss or other indicia within the fibrous structure and/or fibrous product.

"Non-tufted region" as used herein means a region of the fibrous structure and/or fibrous product that is not extended from the fibrous structure and/or fibrous product along the z-axis.

"Chemically different" as used herein means that the chemical compositions of the fibrous structure and/or fibrous product are not the same. For example, one chemical composition may comprise a cellulosic fiber and another chemical composition may comprise a polyethylene terephthalate fiber. In one example, chemically different as in chemically different compositions means that a web made from one composition exhibits a different extensibility, such as a different Stretch at Peak Load as measured by the Stretch at Peak Load Test Method described herein than another web made from a chemically different composition. The stretch difference may be greater than 5% and/or greater than 10% and/or greater than 25% and/or greater than 40% and/or greater than 50%.

The chemically different compositions of the present invention may be in the forms of "layers" thus forming a "layered" fibrous structure and/or fibrous product.

"Layered" as in "layered fibrous structure" means a physical structure that comprises at least two chemically different compositions. In one example, at least one of the at two chemically different compositions comprises a fiber. The at least two chemically different compositions may be integrated with one another in a unitary physical structure thus forming a single ply or single precursor web prior to subjecting the single ply or precursor web to a tuft generating process. Those of skill in the art of fibrous structures, especially cellulosic fibrous structures such as conventional tissue, understand that a layered fibrous structure (one individual ply) is different from a laminate fibrous product (two or more individual plies). Those of skill in the art also know that a layered fibrous structure can form one or more individual plies of a laminate fibrous structure. Various analytical instruments and/or procedures may be employed to facilitate the determination as to whether a fibrous structure is an individual layered fibrous structure or a combination of two or more individual plies. Such instruments/procedures include SEM and/or light microscopy.

Layered, as defined herein means layered in the Z-direction of the fibrous structure and/or product and also, layered in the X-Y direction of the fibrous structure and/or product. In other words, layered as used herein means that the fibrous structure and/or fibrous product of the present invention comprises two or more regions that are chemically different from one another.

A layered fibrous structure of the present invention can be produced by bringing the two chemically different compositions together to form a unitary physical structure and/or integrating one of the compositions in a non-ply form with the other composition, when the other composition is already in the form of a physical structure, such as a ply. One example of this is meltblowing and/or spunbonding and/or otherwise depositing a thermoplastic polymer onto an existing cellulosic web. The thermoplastic polymer, at the time of the deposition step is not in the form of a precursor web, A layered fibrous structure is not a multi-ply fibrous product wherein two, separate discrete pre-formed plies or webs are brought into contact with one another via bonding, or other means of attachment. This does not exclude an example wherein the layered fibrous structure of the present invention is a ply that is combined with another ply of a material.

"Extensibility" as in "extensibility of a chemically different composition, which may be in the form of a layer" is determined according to the Stretch at Peak Load Test Method described herein.

"Integral" as used herein means a portion of the fibrous structure and/or fibrous product that was present in the fibrous structure and/or fibrous product upon original formation of the fibrous structure and/or fibrous product. In other words, an "integral" portion is not a portion of a fibrous structure and/or fibrous product that was added subsequent to the original formation of the fibrous structure and/or fibrous product. For example, an "integral" portion of a fibrous structure and/or fibrous product is to be distinguished from a portion of the fibrous structure and/or fibrous product, such as fibers, introduced to or added to the originally formed fibrous structure and/or fibrous product for the purpose of making tufts, as is conmmonly done in conventional carpet making.

"Ply" or "Plies" as used herein means a single fibrous structure and/or fibrous product optionally to be disposed in a substantially contiguous, face-to-face relationship with other plies, forming a multi-ply web product. It is also contemplated that a single fibrous structure and/or fibrous product can effectively form two "plies" or multiple "plies", for example, by being folded on itself. Ply or plies can also exist as films or other polymeric structures.

"Basis Weight" as used herein is the weight per unit area of a sample reported in lbs/3000 ft$^2$ or g/m$^2$. Basis weight is measured by preparing one or more samples of a certain area (m$^2$) and weighing the sample(s) of a layered fibrous product and/or film according to the present invention on a top loading balance with a minimum resolution of 0.01 g. The balance is protected from air drafts and other disturbances using a draft shield. Weights are recorded when the readings on the balance become constant. The average weight (g) is calculated and the average area of the samples (m$^2$) is measured. The basis weight (g/m$^2$) is calculated by dividing the average weight (g) by the average area of the samples (m$^2$).

"Caliper" or "Sheet Caliper" as used herein means the macroscopic thickness of a single-ply fibrous structure and/or fibrous product, web product or film according to the present invention. Caliper of a fibrous structure and/or fibrous product, web product or film according to the present invention is determined by cutting a sample of the fibrous structure and/or fibrous product, web product or film such that it is larger in size than a load foot loading surface where the load foot loading surface has a circular surface area of about 3.14 in$^2$. The sample is confined between a horizontal flat surface and the load foot loading surface. The load foot loading surface applies a confining pressure to the sample of 15.5 g/cm$^2$ (about 0.21 psi). The caliper is the resulting gap between the flat surface and the load foot loading surface. Such measurements can be obtained on a VIR Electronic Thickness Tester Model II available from Thwing-Albert Instrument Company, Philadelphia, Pa. The caliper measurement is repeated and recorded at least five (5) times so that an average caliper can be calculated. The result is reported in millimeters.

In one example, the single-ply fibrous structure and/or fibrous product and/or sanitary tissue product according to the present invention exhibits a sheet caliper of at least about 0.508 mm (20 mils) and/or at least about 0.762 mm (30 mils) and/or at least about 1.524 mm (60 mils).

"Effective Caliper" as used herein means the radial thickness a layer of fibrous structure and/or sanitary tissue product occupies within a convolutely wound roll of such fibrous structure and/or sanitary tissue product. In order to facilitate the determination of effective caliper, an Effective Caliper Test Method is described herein. The effective caliper of a fibrous structure and/or sanitary tissue product can differ from the sheet caliper of the fibrous structure and/or sanitary tissue product due to winding tension, nesting of deformations, etc.

"Apparent Density" or "Density" as used herein means the basis weight of a sample divided by the caliper with appropriate conversions incorporated therein. Apparent density used herein has the units g/cm$^3$.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Plasticity" as used herein means at least that a material within the fibrous structure and/or fibrous product exhibits a capability of being shaped, molded and/or formed.

"Peak Stretch" as used herein is defined by the following formula:

$$\frac{\text{Length of Web structure}_{WL} - \text{length of Web structure}_I}{\text{Length of Web structure}_I} \times 100\%$$

wherein:

Length of Web structure$_{WL}$ is the length of the web structure at peak load;

Length of Web structure$_I$ is the initial length of the web structure prior to stretching.

The Strength of the Web structure is determined by measuring a web structure's Total Dry Tensile Strength (both MD and CD) or "TDT" using ASTM Standard D828. TDT or Stretch is measured by providing one (1) inch by five (5) inch (2.5 cm×12.7 cm) strips of the web structure in need of testing. Each strip is placed on an electronic tensile tester Model 1122 commercially available from Instron Corp., Canton, Mass. The crosshead speed of the tensile tester is 4.0 inches per minute (about 10.16 cm/minute) and the gauge length is 4.0 inch (about 10.16 cm). The tensile tester calculates the stretch at Peak Load and the stretch at Failure Load. Basically, the tensile tester calculates the stretches via the formulae described above. The Stretch at Peak Load, as used herein, is the average of the Stretch at Peak Load for MD and CD. The Stretch at Failure Load, as used herein, is the average of the Stretch at Failure Load for MD and CD.

"Machine direction" (or MD) is the direction parallel to the flow of the fibrous structure and/or fibrous product and/or precursor fibrous structure being made through the manufacturing equipment.

"Cross machine direction" (or CD) is the direction perpendicular to the machine direction and parallel to the general plane of the fibrous structure and/or fibrous product and/or layered fibrous structure.

"Thermoplastic polymer" as used herein means any material that softens when subjected to heat and hardens during subsequent cooling. "Thermoplastic polymer composition" as used herein means a polymer that melts before decomposing. For example, a thermoplastic polymer can melt in plasticizer and then can be cooled (removal of heat) during a fiber forming process.

Processes of the Present Invention

The processes of the present invention relate to producing polymeric structures such as fibers and/or films from a polymer melt composition comprising a hydroxyl polymer and a crosslinking system and/or to producing web structures comprising a polymeric structure comprising a crosslinked, hydroxyl polymer.

In one nonlimiting example of a process in accordance with the present invention, as described below, a polymer melt composition comprising a hydroxyl polymer and a crosslinking system is polymer processed to form a polymeric structure. During and/or subsequent to the polymer processing step, the crosslinking system crosslinks the hydroxyl polymer to produce a physical structure; namely, a polymeric structure. The polymeric structure can then be incorporated into a web structure. The web structure can then be subjected to a tuft generating process such that a web structure comprising a tufted region and a non-tufted region is produced.

Any suitable process known to those skilled in the art can be used to produce the polymer melt composition and/or to polymer process the polymer melt composition and/or to produce the polymeric structure of the present invention. Nonlimiting examples of such processes are described in published applications: EP 1 035 239, EP 1 132 427, EP 1 217 106, EP 1 217 107, WO 03/066942 and U.S. Pat. No. 5,342,225.

A. Polymer Melt Composition

"Polymer melt composition" as used herein means a composition that comprises a melt processed hydroxyl polymer, such as a hydroxyl polymer. In addition to the melt processed hydroxyl polymer composition, the polymer melt composition may comprise thermoplastic polymers and/or crosslinking systems. "Melt processed hydroxyl polymer" as used herein means any hydroxyl polymer that has been melt processed, with or without the aid of an external plasticizer and/or with or without the presence of a pH adjusting agent. In one example, the hydroxyl polymer contains greater than 10% and/or greater than 20% and/or greater than 25% by weight hydroxyl groups. More generally, melt processed hydroxyl polymers include polymers, which by the influence of elevated temperatures, pressure and/or external plasticizers may be softened to such a degree that they can be brought into a flowable state (all melt processing operations/processes), and in this condition may be shaped as desired.

The hydroxyl polymer melt composition may be a composite containing a blend of different polymers, wherein at least one is a melt processed hydroxyl polymer according to the present invention, and/or fillers both inorganic and organic, and/or fibers and/or foaming agents. In one example, the hydroxyl polymer melt composition comprises two or more different melt processed non-thermoplastic polymers according to the present invention. As used herein, "different melt processed non-thermoplastic polymers" includes without limitation, melt processed hydroxyl polymers that contain at least one different moiety relative to another melt processed hydroxyl polymer and/or melt processed hydroxyl polymers that are members of different chemical classes (e.g., PVOH versus starch versus chitosan).

The hydroxyl polymer melt composition may already be formed or a melt processing step may need to be performed to convert a hydroxyl polymer into a melt processed hydroxyl polymer, thus producing the hydroxyl polymer melt composition. Any suitable melt processing step known in the art may be used to convert the raw material hydroxyl polymer into the melt processed hydroxyl polymer.

The hydroxyl polymer melt composition may comprise by weight a) from about 30% and/or 40% and/or 45% and/or 50% to about 75% and/or 80% and/or 85% and/or 90% and/or 99.5% of a hydroxyl polymer; b) a crosslinking system comprising from about 0.1% to about 10% by weight of the hydroxyl polymer melt composition of a crosslinking agent; and c) from about 0% and/or 10% and/or 15% and/or 20% to about 50% and/or 55% and/or 60% and/or 70% by weight of the hydroxyl polymer melt composition of an external plasticizer (e.g., water).

B. Polymer Processing

"Polymer processing" as used herein means any operation and/or process by which a polymeric structure comprising a processed hydroxyl polymer is formed from a hydroxyl polymer melt composition. Nonlimiting examples of polymer processing operations include extrusion, molding and/or fiber spinning. Extrusion and molding (either casting or blown), typically produce films, sheets and various profile extrusions. Molding may include injection molding, blown molding and/or compression molding. Fiber spinning may include spun bonding, melt blowing, continuous fiber producing and/or tow fiber producing.

A "processed hydroxyl polymer" as used herein means any hydroxyl polymer that has undergone a melt processing operation and a subsequent polymer processing operation.

C. Polymeric Structure

The hydroxyl polymer melt composition can be subjected to one or more polymer processing operations such that the non-thernoplastic polymer melt composition is processed into a polymeric structure such as a fiber or a film comprising the hydroxyl polymer and a crosslinking system according to the present invention.

Post Treatment of Polymeric Structures

Once the hydroxyl polymer melt composition has been processed into a polymeric structure, such as a fiber, a film or a plurality of fibers that together form a web structure, the polymeric structure and/or web structure comprising such polymeric structure may be subjected to post-treatment curing and/or differential densification.

In one example, the structure produced via a polymer processing operation may be cured at a curing temperature of from about 110° C. to about 215° C. and/or from about 110° C. to about 200° C. and/or from about 120° C. to about 195° C. and/or from about 130° C. to about 185° C. for a time period of from about 0.01 and/or 1 and/or 5 and/or 15 seconds to about 60 minutes and/or from about 20 seconds to about 45 minutes and/or from about 30 seconds to about 30 minutes prior to densifying a region of the structure. Alternative curing methods may include radiation methods such as UV, e-beam, IR and other temperature-raising methods.

Further, the structure may also be cured at room temperature for days, either after curing at above room temperature or instead of curing at above room temperature.

The web structure of the present invention may be subjected to differential densification via a differentially densifying operation. Such differential densification can occur on-line in a continuous process that includes forming the structure and then differentially densifying the structure. Alternatively, the differential densification can occur off-line in a non-continuous process. Differentially densifying the web structure produces two or more regions within the web structure that exhibit different densities as compared to one another.

Any differentially densifying process known to those of ordinary skill in the art may be used to differentially densify the structures of the present invention.

Curing of the web structure may occur before and/or after differentially densifying.

The web structure, prior to being densified, may comprise non-associated substantially continuous or continuous fibers.

The web structure may comprise from about 10% and/or from about 15% and/or from about 20% to about 60% and/or to about 50% and/or to about 40% by weight of the structure of moisture.

Like the tuft generating process described herein, the differentially densifying process may comprise a step of imparting plasticity into the web structure such two or more regions of differential density can be produced in the web structure by a pattern. Exposing the web structure in need of differential densification to a humid environment, such as from about 20% to about 95% and/or from about 40% to about 90% and/or from about 50% to about 85% and/or from about 65% to about 80% relative humidity for a sufficient time, such as at least 1 second and/or at least 3 seconds and/or at least 5 seconds, can impart sufficient plasticity to the web structure to permit differential densification to be created in the structure.

In one example, the differentially densifying process comprises subjecting the structure to a patterned roller such that the pattern on the roller is imparted to the structure, thus causing the structure to become differentially densified.

In another example, the differentially densifying process comprises contacting the structure, which is in contact with a patterned belt/fabric with pressure from a smooth roller thus imparting the pattern of the belt/fabric to the structure causing the structure to become differentially densified.

The differentially densifying of a structure in accordance with the present invention preferably occurs after the structure has been formed, not concurrent with the formation of the structure.

The structure of the present invention may be differentially densified more than once. For example, a structure may be differentially densified, then cured, and then differentially densified again according to the present invention.

In another example, the structure may comprise two or more "plies" of structure which can then be differentially densified as a multi-ply structure.

The structure may be differentially densified, then differential densified again and then cured.

Alternatively, the structure of the present invention may be cured, then differentially densified according to the present invention Curing of the structure, in accordance with the present invention, may occur at any point in time relative to any differentially densifying process. It may occur before (preferably immediately before), after (preferably immediately after), before and after (preferably immediately before and immediately after), or not at all.

The differentially densifying process may occur once or a plurality of times.

Ultrasonics may also be used to aid in differential densification of the structure, especially in conjunction with a patterned roller. The ultrasonics may be generated by any suitable ultrasonic device. For example, a horn or ultrasonic wave generator that is capable of imparting energy to the structure such that the structure deforms according to the pattern on the patterned roller can be used.

In still another example, the step of differentially densifying comprises contacting the web structure with a structure-imparting element comprising a pattern in the presence of humidity and applying a force to the web structure and/or structure-imparting element such that the web structure takes the shape of the pattern on the structure-imparting element to form a differential densified polymeric structure.

In yet still another example, the step of differentially densifying the web structure comprises sandwiching the web structure between two belts in the presence of humidity, wherein at least one of the belts is a structured belt comprising a pattern and applying a force to at least one of the belts such that the web structure takes the shape of the pattern on the structured belt to form a differential densified polymeric structure.

Hydroxyl Polymers

Hydroxyl polymers may comprise any suitable hydroxyl polymer known in the art. More particularly, the hydroxyl polymers of the present invention may include any suitable hydroxyl polymer that is capable of being crosslinked by a crosslinking system such that a polymeric structure comprising the crosslinked, hydroxyl polymer is formed.

Hydroxyl polymers in accordance with the present invention include any hydroxyl-containing polymer that can be incorporated into a polymeric structure of the present invention.

In one example, the hydroxyl polymer of the present invention includes greater than 10% and/or greater than 20% and/or greater than 25% by weight hydroxyl moieties.

Nonlimiting examples of suitable hydroxyl polymers in accordance with the present invention include polyols, such as polyvinyl alcohol, polyvinyl alcohol derivatives, starch, starch derivatives, chitosan, chitosan derivatives, cellulose derivatives such as cellulose ether and ester derivatives, gums, arabinans, galactans, proteins and various other polysaccharides and mixtures thereof.

With regard to the starch derivative, well known modifications of natural starches can include chemical modifications and/or enzymatic modifications. For example, the natural starch can be acid-thinned, hydroxy-ethylated or hydroxy-propylated or oxidized.

"Polysaccharides" herein means natural polysaccharides and polysaccharide derivatives or modified polysaccharides. Suitable polysaccharides include, but are not limited to, gums, arabinans, galactans and mixtures thereof.

The hydroxyl polymers, especially hydroxyl polymers, may have a weight average molecular weight of from about 10,000 to about 40,000,000 g/mol and/or from about 10,000 to about 10,000,000 g/mol. Higher and lower molecular weight hydroxyl polymers may be used in combination with hydroxyl polymers having a weight average molecular weight of between about 10,000 to about 40,000,000 g/mol.

Crosslinking System

The crosslinking system comprises a crosslinking agent and optionally, a crosslinking facilitator.

"Crosslinking facilitator" as used herein means any material that is capable of activating a crosslinking agent to initiate the crosslinking of the hydroxyl polymer.

The crosslinking facilitator may include derivatives of the material that may exist after the transformation/activation of the crosslinking agent. For example, a crosslinking facilitator salt being chemically changed to its acid form and vice versa.

A crosslinking system may be present in the hydroxyl polymer melt composition and/or may be added to the hydroxyl polymer melt composition before polymer processing of the hydroxyl polymer melt composition.

Nonlimiting examples of suitable crosslinking facilitators include acids having a pKa of between about 0 and about 6 and/or between about 1.5 and about 6 and/or between about 2 and about 6 or salts thereof. The crosslinking facilitators may be Bronsted Acids and/or salts thereof, preferably ammonium salts thereof.

In addition, metal salts, such as magnesium and zinc salts, can be used alone or in combination with Bronsted Acids and/or salts thereof, as crosslinking facilitators.

Nonlimiting examples of suitable crosslinking facilitators include acetic acid, benzoic acid, citric acid, formic acid, glycolic acid, lactic acid, maleic acid, phthalic acid, phosphoric acid, sulfuric acid, succinic acid, oxalic acid, tartaric acid, malic acid, hydrochloric acid, nitric acid, fluoboric acid and mixtures thereof and/or their salts, preferably their ammonium salts, such as ammonium glycolate, ammonium citrate and ammonium sulfate.

Nonlimiting examples of suitable crosslinking agents include polycarboxylic acids, imidazolidinones and other compounds resulting from alkyl substituted or unsubstituted cyclic adducts of glyoxal with ureas, thioureas, guanidines, methylene diamides, and methylene dicarbamates and derivatives thereof; and mixtures thereof.

Web Structure

As shown in FIG. 1A, in one example, a web structure 10 in accordance with the present invention comprises a tuft 12, wherein the web structure 10 further comprises a polymeric structure comprising crosslinked, hydroxyl polymer. In this case, the polymeric structure can be a film or a fiber (not shown). The tuft 12 may comprise the polymeric structure. The web structure 10 may comprise a single tuft 12 or a plurality of tufts 12. The tuft 12 extends from the web structure 10 along the z-axis. The web structure 10 is formed from a generally planar (x-y plane), two dimensional nonwoven precursor web structure. The web structure 10 comprises a first surface 14 and a second surface 16. The web structure 10 has a machine direction (MD) and a cross machine direction (CD) as is commonly known in the art of nonwoven web structures. First surface 14 corresponds to first "side" 18 of web structure 10 and second surface 16 corresponds to the second "side" 20 of web structure 10, the term "sides" being used in the common usage of generally two-dimensional web structures, such as paper and films. Although the present invention can be practiced with woven web structures, in this example, the precursor web is a nonwoven web structure and is comprised of substantially randomly oriented fibers, that is, randomly oriented at least with respect to the MD and CD. By "substantially randomly oriented" is meant that, due to processing conditions, there may be a higher amount of fibers oriented in the MD than the CD, or vice-versa. For example, in spunbonding and meltblowing processes, continuous strands of fibers are deposited on a support moving in the MD. Despite attempts to make the orientation of the fibers of the spunbond or meltblown nonwoven web "random," usually a higher percentage of fibers are oriented in the MD as opposed to the CD.

The nonwoven precursor web structure (not shown) can be any known nonwoven web structure comprising a polymeric structure in the form of a film or a fiber, wherein the nonwoven web structure exhibits sufficient elongation properties to be formed into web structure 10 as described more fully below.

Figure 1B:
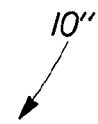
FIG. 1B is a cross-section view of section B-B of FIG. 1.

As shown in FIG. 1B, the tuft 12 creates a discontinuity 22 in the web structure 10 along the second "side" 20. As a result of the formation of the tuft 12 an open void area 24 may be defined by the tuft 12.

Figure 2A:
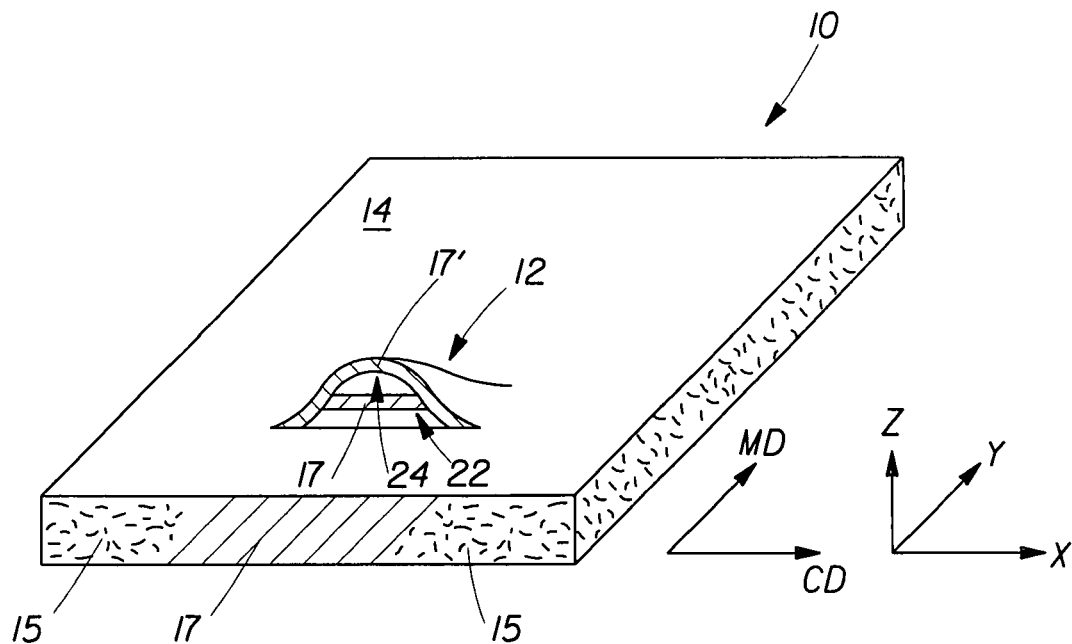
FIG. 2A is a schematic representation of a web structure of the present invention.

As shown in FIG. 2A, a web structure 10 of the present invention may comprise a first region 15 and a second region 17 and a surface of the fibrous product 14, wherein the first region 15 comprises a first composition and the second region 17 comprises a second composition, wherein the first and second compositions are chemically different such that the first region 15 exhibits an extensibility different from the second region 17, wherein a portion of one region, such as a portion of the second region 17', less than all of the chemically different compositions forms a tuft 12 on the surface of the fibrous product 14, wherein the web structure comprises a polymeric structure comprising a crosslinked, hydroxyl polymer. For illustration purposes, only a single tuft is shown. However, the present invention encompasses fibrous structures and/or fibrous products that comprise a surface that comprises one or more tufts.

Figure 2B:
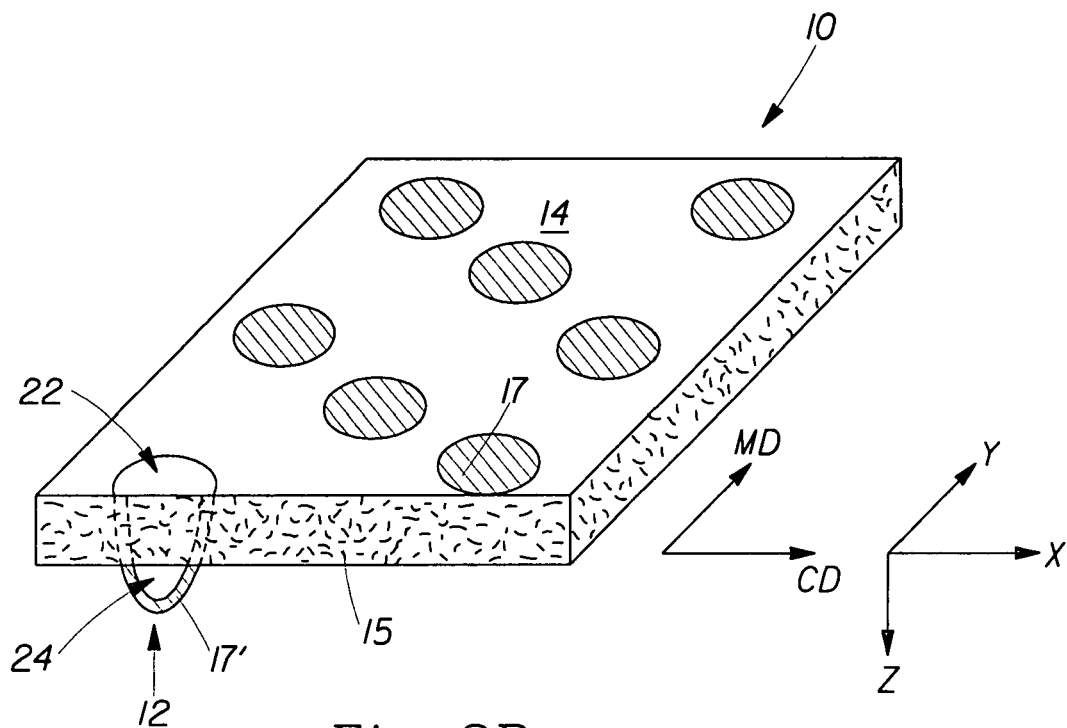
FIG. 2B is a schematic representation of a web structure of the present invention.

As shown in FIG. 2B, a fibrous structure and/or fibrous product 10 of the present invention may comprise a first layer 15 and a second layer 17, wherein the second layer 17 is present on the surface 14 of the fibrous structure and/or fibrous product 10 in the form of discrete regions. The first layer 15 comprises a first composition and the second layer 17 comprises a second composition, wherein the first and second compositions are chemically different such that the first layer 15 exhibits an extensibility different from the second layer 17, wherein a portion of one layer, such as a portion of the second layer 17', less than all of the chemically different compositions forms a tuft 12 on the surface of the fibrous product 14, wherein the web structure comprises a polymeric structure comprising a crosslinked, hydroxyl polymer. For illustration purposes, only a single tuft is shown. However, the present invention encompasses fibrous structures and/or fibrous products that comprise a surface that comprises one or more tufts.

The tuft 12 may comprise a polymeric structure. The polymeric structure may be a fiber and/or a film. The tuft 12 may comprise one fiber or a plurality of fibers, as shown in FIG. 3.

The tuft 12 may comprise a crosslinked, hydroxyl polymer. When fibers are present in the tuft 12 the fibers may comprise a crosslinked, hydroxyl polymer.

Figure 3:
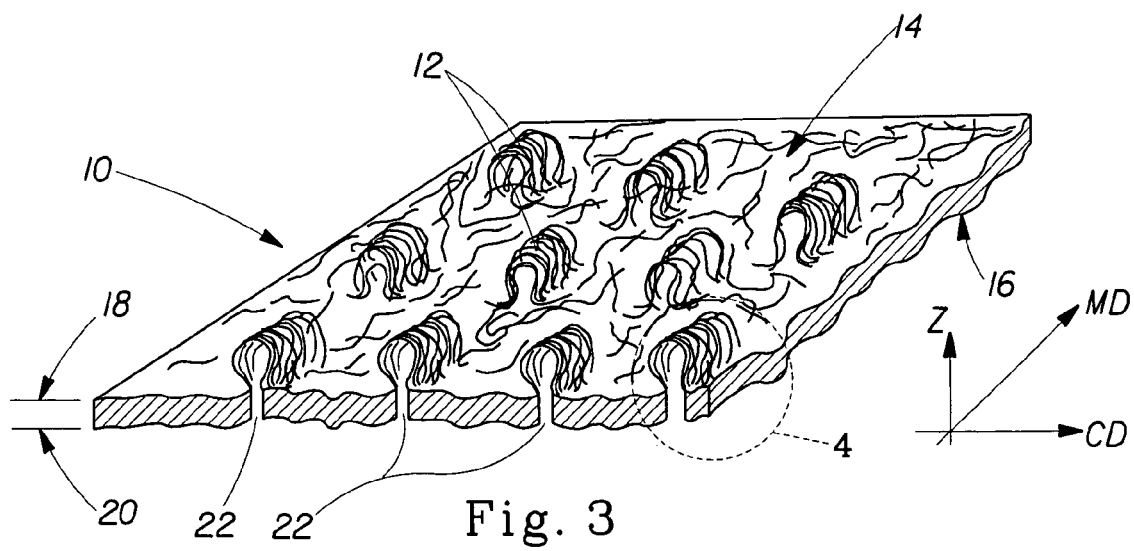
FIG. 3 is a perspective view of a web structure of the present invention.
Figure 4:
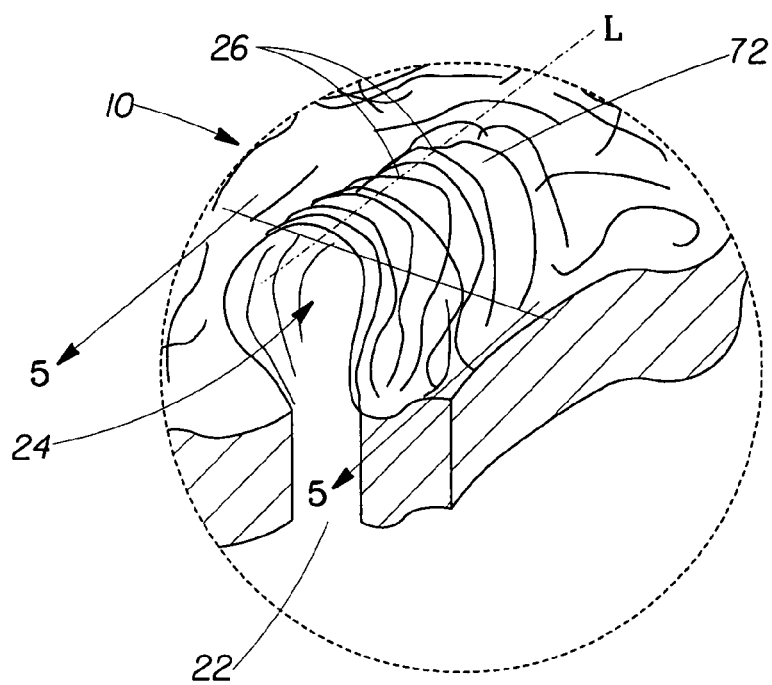
FIG. 4 is an enlarged view of a portion of the web structure shown in FIG. 3.
Figure 5:
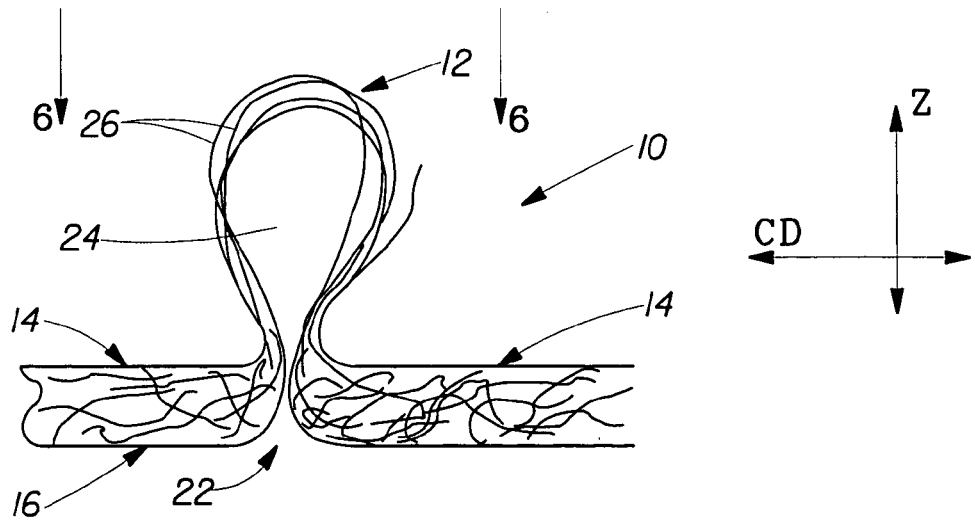
FIG. 5 is a cross-sectional view of section 5-5 of FIG. 4.
Figure 6:
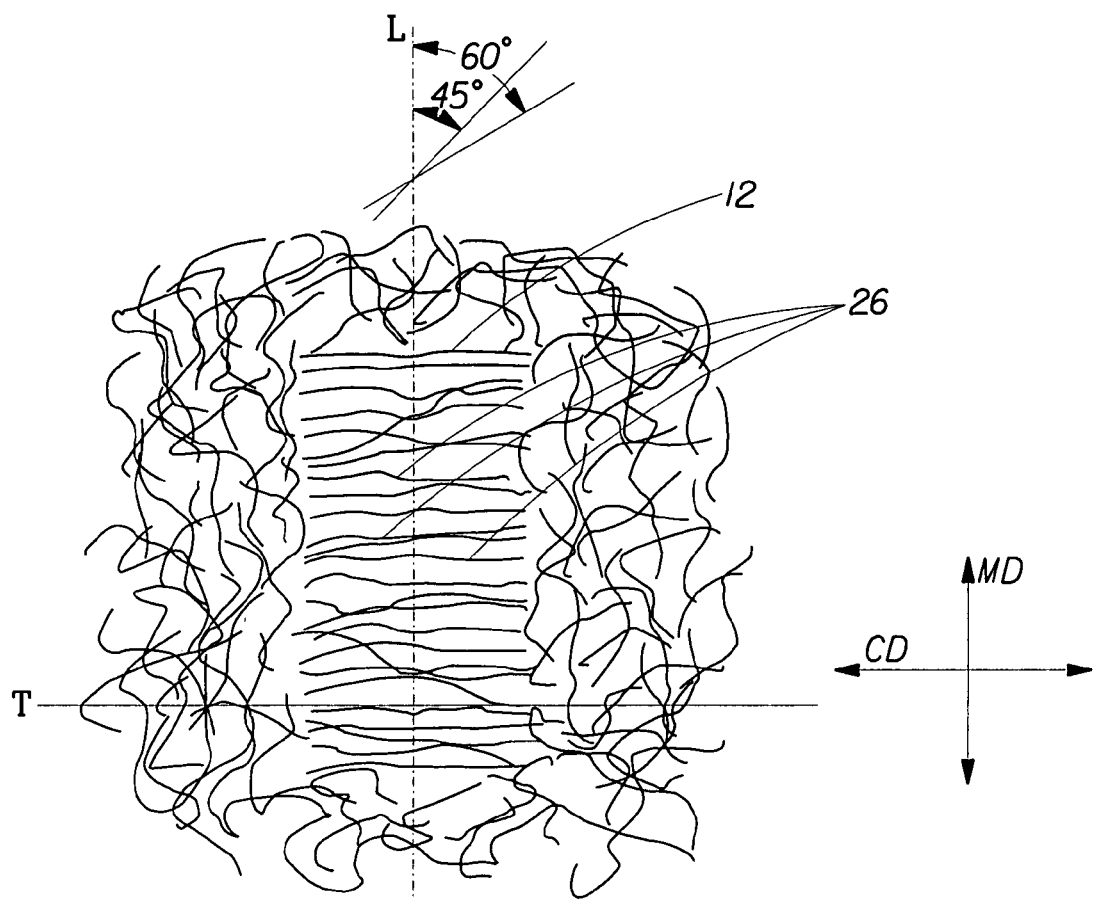
FIG. 6 is a plan view of a portion of the web structure of FIG. 3.

FIGS. 4 and 5 schematically illustrate an enlarged view of a tuft 12 from one example of the web structure 10 shown in FIG. 3. As shown, tuft 12 comprises a plurality of looped fibers 26 that are substantially aligned such that tuft 12 has a distinct longitudinal orientation and a longitudinal axis L. Tuft 12 also has a transverse axis T generally orthogonal to longitudinal axis L in the MD-CD plane, as shown in FIG. 6. In one example, as shown in FIG. 3, all of the spaced apart tufts 12 have generally parallel longitudinal axes L. The number of tufts 12 per unit area of web structure 10, i.e., the area density of tufts 12, can be nonlimitingly varied from 1 tuft 12 per square centimeter to as high as 100 tufts 12 per square centimeter. There can be at least 10, or at least 20 tufts 12 per square centimeter, depending on the end use. In general, the area density need not be uniform across the entire area of the web structure 10, but tufts 12 can be only in certain regions of the web structure 10, such as in regions having predetermined shapes, such as lines, stripes, bands, circles, and the like.

As shown in FIGS. 4 and 6, one characteristic of the fibers 26 of tufts 12 in one example of the web structure 10 is the predominant directional alignment of the tufted fibers 26. As shown in FIG. 6, the tufted fibers 26 have a substantially uniform alignment with respect to transverse axis T when viewed in plan view. By "tufted" fibers 26 is meant that fibers 26 begin and end in the web structure 10. By "aligned" with respect to tufted fibers 26 of tufts 12 is meant that tufted fibers 26 are all generally oriented such that, if viewed in plan view as in FIG. 6, each of the tufted fibers 26 has a significant vector component parallel to the transverse axis T, and preferably a major vector component parallel to the transverse axis T. As used herein, a tufted fiber 26 oriented at an angle of greater than 45 degrees from the longitudinal axis L when viewed in plan view, as in FIG. 6, has a significant vector component parallel to the transverse axis T. As used herein, a tufted fiber 26 oriented at an angle of greater than 60 degrees from longitudinal axis L when viewed in plan view, as in FIG. 6, has a major vector component parallel to the transverse axis T. In a preferred example, at least 50%, more preferably at least 70%, and more preferably at least 90% of the tufted fibers 26 of tuft 12 have a significant, and more preferably, a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the tufted fibers 26 can be used for determining the angle of the tufted fibers 26 from longitudinal axis L.

The orientation of tufted fibers 26 in the tufts 12 is to be contrasted with the fiber composition and orientation of the non-tufted region of the web structure 10, which, for nonwoven precursor webs is best described as having a substantially randomly-oriented fiber alignment. In a woven web example, the orientation of the tufted fibers 26 in tufts 12 could be the same as described above, but the fibers of the tuft would have the orientation associated with the particular weaving process used to make the web, e.g., a square weave pattern.

From the description of the web structure 10, it can be seen that the tufted fibers 26 of tuft 12 can originate and extend from either the first surface 14 and/or the second surface 16 of the web structure 10. Of course the tufted fibers 26 of tuft 12 can also extend from the interior 28 of the precursor nonwoven web as shown in FIG. 5. The tufted fibers 26 of tufts 12 extend due to having been urged out of the generally two-dimensional plane (x-y plane) of the nonwoven precursor web. In general, the tufted fibers 26 of the tuft 12 comprise fibers that are integral with and extend from the non-tufted fibers of the web structure 10.

Even though the discussion of the web structure examples herein is focused on web structures that comprise a polymeric structure in the form of a fiber, web structures that comprise a polymeric structure in the form of a film are also covered. The tuft of the web structure may comprise a fiber or a portion of a fiber and/or a film or portion of a film. The tuft may comprise a polymeric structure that comprises a crosslinked, hydroxyl polymer wherein the polymeric structure is in the form of a fiber and/or a film.

The tuft of the web structures of the present invention may comprise any suitable material so long as the material of the tuft exhibits sufficient stretch to be deformed in the tuft generating process. In other words, the material of the tuft must have a stretch at peak load that is sufficient to permit deformation of the material into the tuft during the tuft generating process. In one example, the material exhibits a stretch at peak load before formation, as measured by the Stretch at Peak Load test described herein, of the tuft of at least about 1% and/or at least about 3% and/or at least about 5%. The material after tuft formation may also exhibit such a stretch or it may not.

In one example, the tuft comprises a polymeric structure comprising a crosslinked, hydroxyl polymer that is capable of exhibiting a sufficient stretch to form a tuft when the material is exposed to a plasticizing environment, such as sufficient relative humidity to soften the crosslinked, hydroxyl polymer to at least a point wherein the material can form a tuft during a tuft generating process.

In another example, the web structure of the present invention comprises a tufted region and a non-tufted region, wherein the tufted region comprises a tuft and wherein the tufted region is integral with but extends from the non-tufted region, wherein the web structure comprises a polymeric structure comprising a crosslinked, hydroxyl polymer.

In yet another example, the web structure of the present invention comprises a first region and at least one discrete integral second region, the second region having at least one portion being a discontinuity and at least another portion being a deformation comprising at least one tuft integral with but extending from the first region, wherein the web structure comprises a polymeric structure comprising a crosslinked, hydroxyl polymer.

In even yet another example, the web structure comprises a first region and at least one discrete integral second region, the second region having at least one portion being a discontinuity exhibiting a linear orientation and defining a longitudinal axis (L) and at least another portion being a deformation comprising at least one tufted fiber integral with but extending from the first region, wherein the web structure comprises a polymeric structure comprising a crosslinked, hydroxyl polymer.

In even still another example, a multi-ply web product comprises a first web ply and a second web ply, at least one of the first web ply and second web ply comprises a web structure and/or a layered web structure in accordance with the present invention.

The web structure of the present invention may be combined with an additional web structure, the same or different from the web structure of the present invention. Tufts present in the web structure of the present invention may protrude at least into the additional web structure. In addition, the tufts present in the web structure of the present invention may protrude through the additional web structure as a result of the addition web structure breaking at the point of the tuft.

The additional web structure may be combined with the web structure of the present invention by any suitable means. The web structures may be combined before or after tufts are present in the web structure of the present invention.

The web structure of the present invention and the additional web structure may exhibit different stretch properties at peak load. For example the web structure of the present invention may exhibit a stretch at peak load that is less than the stretch at peak load of the additional web structure.

In another example, a portion of the web structure of the present invention may exhibit a stretch at peak load that is less than the stretch at peak load of the additional web or portions of the additional web. The stretch at peak load of the web structure of the present invention or portions thereof may be influenced, especially immediately before and/or during being subjected to a tuft generating process such that the stretch at peak load of the web structure of the present invention or portions thereof is greater than the stretch at peak load of the additional web structure.

In other examples, the web structure of the present invention or portions thereof may exhibit a greater stretch at peak load than the additional web structure or portions thereof.

The web structures of the present invention may be formed by any suitable process known in the art.

Tuft Generating Process

For examples of the web structures of the present invention wherein the tuft comprises a polymeric structure as described herein, the web structure and/or the polymeric structure within the web structure may be subjected to a plasticizing process. Nonlimiting examples of plasticizing processes for use herein include subjecting the web structure and/or the polymeric structure within the web structure to a humid environment such that the polymeric structure exhibits sufficient plasticity to undergo a tuft generating process without breaking. Nonlimiting examples of suitable humid environments include environments of at least about 40% relative humidity and/or at least about 50% relative humidity and/or at least about 60% relative humidity and/or at least about 75% relative humidity. In one example, water may be applied to the web structure and/or to the polymeric structure within the web structure.

In a multi-ply web structure example, one web structure or portions thereof, such as the polymeric structure within the web structure, in accordance with the present invention may be plasticizable and another web structure combined with the first web structure may not be plasticizable to the same extent. In this case, during the tuft generating process, the plasticizable web structure would form a tuft that protrudes through the other lesser plasticizable web structure such that the lesser plasticizable web structure breaks allowing the tuft to protrude through the web structure.

Figure 7:
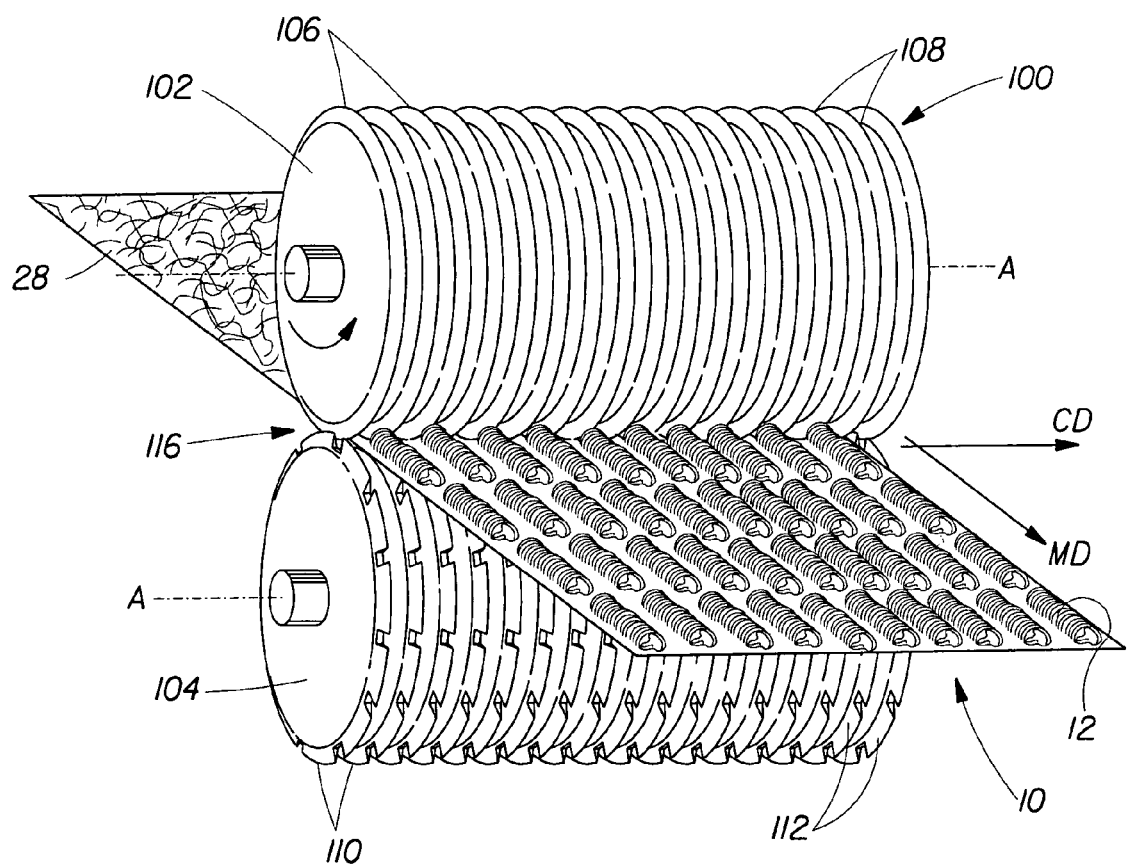
FIG. 7 is a perspective view of an apparatus for forming the web structure of the present invention.

Referring to FIG. 7, there is shown a nonlimiting example of an apparatus and method for making a web structure of the present invention. The apparatus 100 comprises a pair of intermeshing rolls 102 and 104, each rotating about an axis A, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 8, discussed below.

In FIG. 7, the apparatus 100 is shown in a preferred configuration having one patterned roll, e.g., roll 104, and one non-patterned grooved roll 102. However, in certain examples it may be preferable to use two patterned rolls 104 having either the same or differing patterns, in the same or different corresponding regions of the respective rolls. Such an apparatus can produce web structures with tufts protruding from both sides of the web structure.

The process of the present invention is similar in many respects to a process as described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus of the present invention and the apparatus disclosed in the above-identified '801 patent. These differences account for the novel features of the web of the present invention. As described below, the teeth 110 of roll 104 have a specific geometry associated with the leading and trailing edges that permit the teeth, e.g., teeth 110, to essentially "punch" through the precursor web 28 as opposed to, in essence, emboss the web. The difference in the apparatus 100 of the present invention results in a fundamentally different web structure.

Precursor web 28 is provided either directly from a web making process or indirectly from a supply roll (neither shown) and moved in the machine direction to the nip 116 of counter-rotating intermeshing rolls 102 and 104. Precursor web 28 can be any suitable web structure that exhibits or is capable of exhibiting sufficient stretch at peak load to permit formation of tufts in the web structure. Precursor web 28 can be plasticized by any means known in the art, such as by subjecting the precursor web to a humid environment. Furthermore, precursor web 28 can be a nonwoven web made by known processes, such as meltblown, spunbond, rotary spinning and carded. As precursor web 28 goes through the nip 116 the teeth 110 of roll 104 enter grooves 108 of roll 102 and simultaneously urge fibers out of the plane of plane of precursor web 28 to form tufts 12 and discontinuities 22, not shown in FIG. 7. In effect, teeth 110 "push" or "punch" through precursor web 28. As the tip of teeth 110 push through precursor web 28 the portions of fibers that are oriented predominantly in the CD and across teeth 110 are urged by the teeth 110 out of the plane of precursor web 28 and are stretched, pulled, and/or plastically deformed in the z-axis, resulting in formation of the tuft 12. Fibers that are predominantly oriented generally parallel to the longitudinal axis L, i.e., in the machine direction of precursor web 28 as shown in FIG. 7, are simply spread apart by teeth 110 and remain substantially in the non-tufted region of the web structure 10. Although, as discussed more fully below, it has been found that the rate of formation of tufts 12 affects fiber orientation, in general, and at least at low rates of formation, it can be understood why the tufted fibers can exhibit the unique fiber orientation which is a high percentage of fibers having a significant or major vector component parallel to the transverse axis T of tuft 12, as discussed above with respect to FIG. 6. In general, at least some of the fibers of tuft 12 are tufted, aligned fibers 26 which can be described as having a significant or major vector component parallel to a Z-oriented plane orthogonal to transverse axis T.

The number, spacing, and size of tufts can be varied by changing the number, spacing, and size of teeth 110 and making corresponding dimensional changes as necessary to roll 104 and/or roll 102. This variation, together with the variation possible in precursor webs 28 and line speeds, permits many varied web structures to be made for many purposes. For example, a web structure made from a high basis weight textile fabric having MD and CD woven extensible threads could be made into a soft, porous ground covering, such as a cow carpet useful for reducing udder and teat problems in cows. A web structure made from a relatively low basis weight nonwoven web of extensible spunbond polymer fibers could be used as a terry cloth-like fabric for semi-durable or durable clothing.

Figure 8:
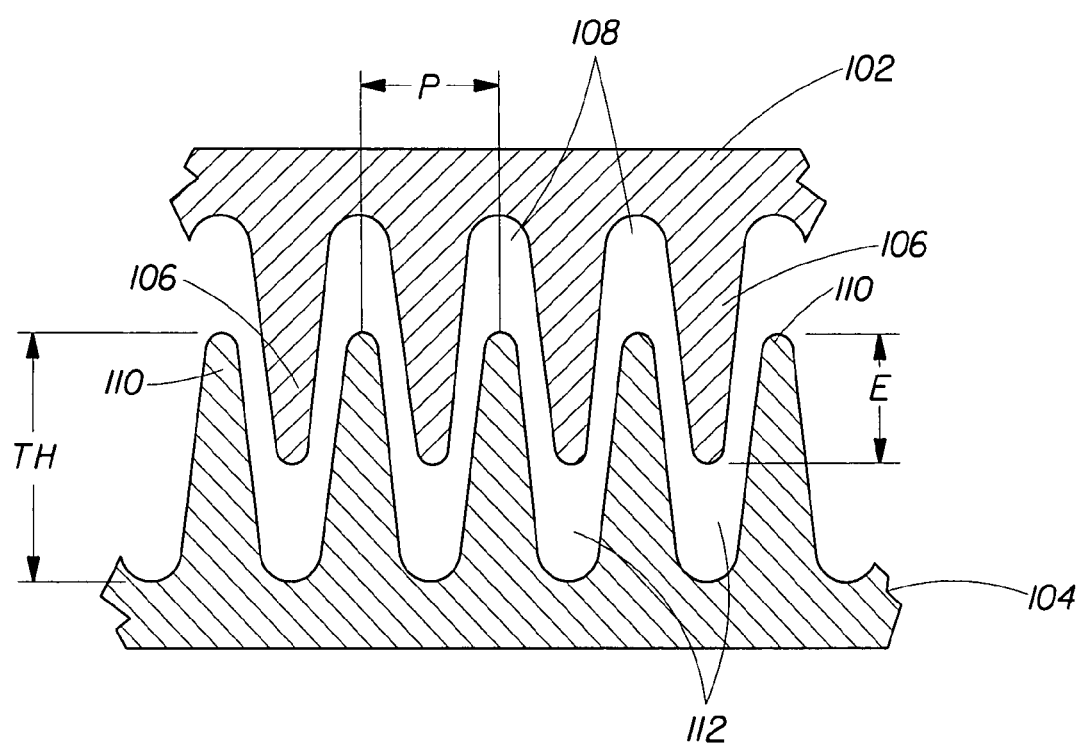
FIG. 8 is a cross-sectional depiction of a portion of the apparatus shown in FIG. 7.

FIG. 8 shows in cross section a portion of the intermeshing rolls 102 and 104 including ridges 106 and teeth 110. As shown teeth 110 have a tooth height TH (note that TH can also be applied to ridge 106 height; in a preferred example tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of the precursor web and the desired characteristics of web structure. For example, in general, to obtain tufted fibers in tuft 12, the greater the level of engagement E, the greater the necessary fiber mobility and/or elongation characteristics the fibers of the precursor web must possess. Also, the greater the density of the tufted regions desired (tufted regions per unit area of web structure), the smaller the pitch should be, and the smaller the tooth length TL and tooth distance TD should be, as described below.

Figure 9:
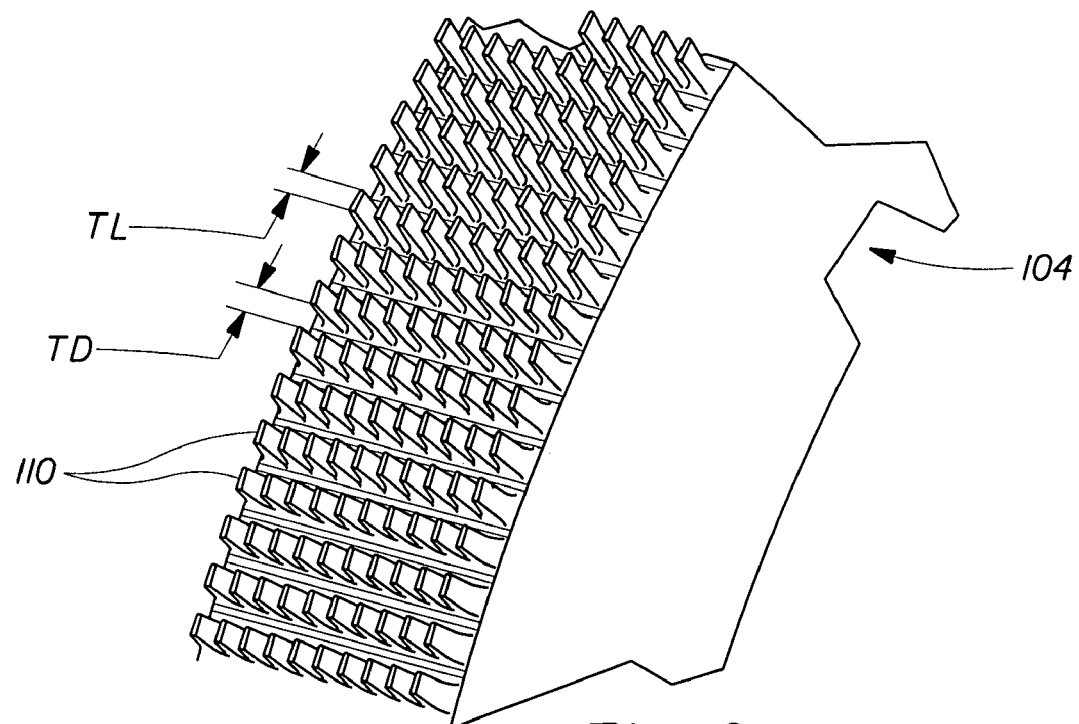
FIG. 9 is a perspective view of a portion of the apparatus for forming one example a web structure of the present invention.
Figure 10:
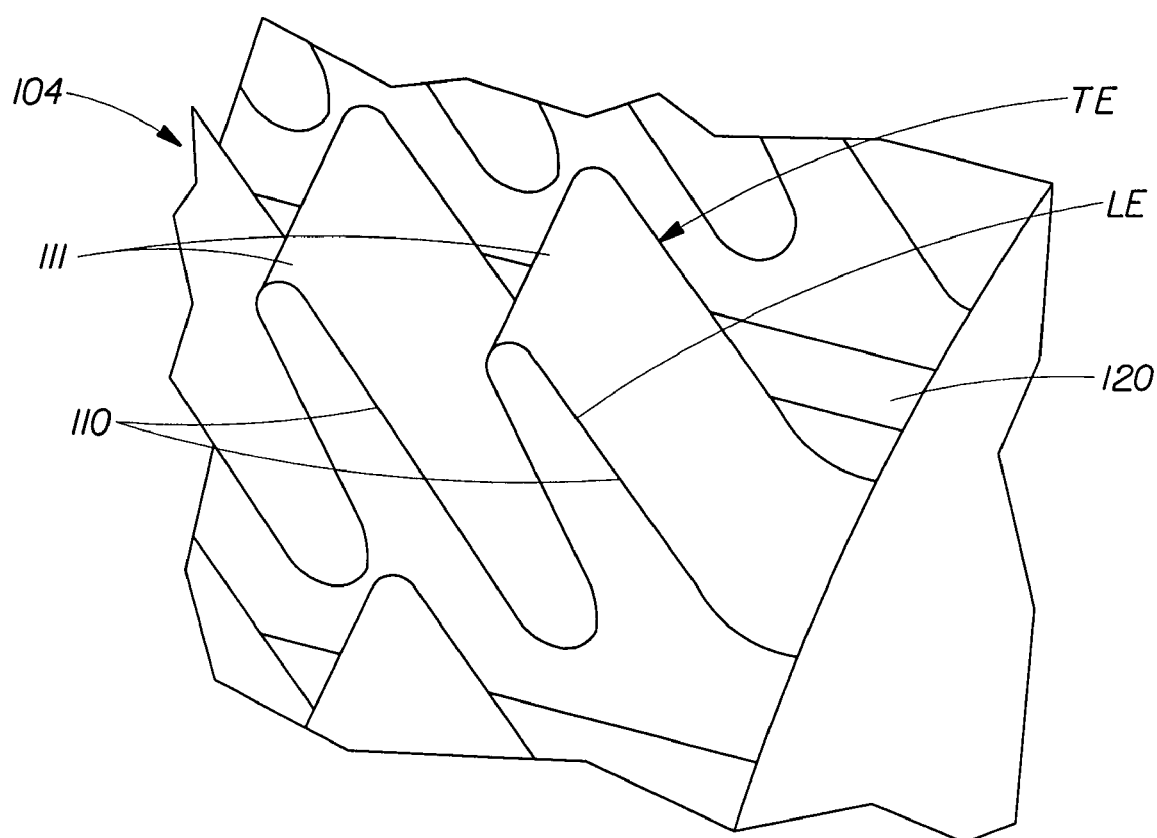
FIG. 10 is an enlarged perspective view of a portion of the apparatus for forming the web structure of the present invention.

FIG. 9 shows one example of a roll 104 having a plurality of teeth 110 useful for making a web structure of the present invention having a basis weight of between about 15 gsm and 100 gsm and/or from about 25 gsm to about 90 gsm and/or from about 30 gsm to about 90 gsm. In one example, the resulting web structure exhibits a basis weight of from about 15 gsm to about 50 gsm and/or from about 15 gsm to about 40 gsm. An enlarged view of teeth 110 shown in FIG. 9 is shown in FIG. 10. In this example of roll 104 teeth 110 have a uniform circumferential length dimension TL of about 1.25 mm measured generally from the leading edge LE to the trailing edge TE at the tooth tip 111, and are uniformly spaced from one another circumferentially by a distance TD of about 1.5 mm. For making a web structure from a precursor web having a basis weight in the range of about 15 gsm to 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 10 mm, and a pitch P between about 1 mm (0.040 inches) and 2.54 mm (0.100 inches). Depth of engagement E can be from about 0.5 mm to about 5 mm (up to a maximum approaching the tooth height TH). Of course, E, P, TH, TD and TL can each be varied independently of each other to achieve a desired size, spacing, and area density of tufts (number of tufts per unit area of web structure).

As shown in FIG. 10, each tooth 110 has a tip 111, a leading edge LE and a trailing edge TE. The tooth tip 111 is elongated and has a generally longitudinal orientation, corresponding to the longitudinal axes L of tufted regions. It is believed that to get the tufts of the web structure that can be described as being terry cloth-like, the LE and TE should be very nearly orthogonal to the local peripheral surface 120 of roll 104. As well, the transition from the tip 111 and the LE or TE should be a sharp angle, such as a right angle, having a sufficiently small radius of curvature such that, in use the teeth 110 push through precursor web at the LE and TE. Without being bound by theory, it is believed that having relatively sharply angled tip transitions between the tip of tooth 110 and the LE and TE permits the teeth 110 to punch through precursor web "cleanly", that is, locally and distinctly, so that the resulting web structure can be described as "tufted" in tufted regions rather than "embossed" for example. When so processed, the web structure is not imparted with any particular elasticity, beyond what the precursor web may have possessed originally.

It has been found that line speed, that is, the rate at which precursor web is processed through the nip of rotating rolls 102 and 104, and the resulting rate of formation of tufts, impacts the structure of the resulting tufts.

Although the web structure of the present invention is disclosed in preferred examples as a single ply web structure made from a single ply precursor web, it is not necessary that it be so. For example, a laminate or composite precursor web having two or more plies can be used. In general, the above description for the web structure holds, recognizing that tufted, aligned fibers, for example, formed from a laminate precursor web would be comprised of fibers from both (or all) plies of the laminate. In such a web structure, it is important, therefore, that all the fibers of all the plies have sufficient diameter, elongation characteristics, and fiber mobility, so as not to break prior to extension and tufting. In this manner, fibers from all the plies of the laminate may contribute to the tufts. In a multilayer web structure, the fibers of the different plies may be mixed or intermingled in the tuft and/or tufted regions. The fibers do not protrude through but combine with the fibers in an adjacent ply. This is often observed when the plies are processed at very high speeds.

Figure 11:
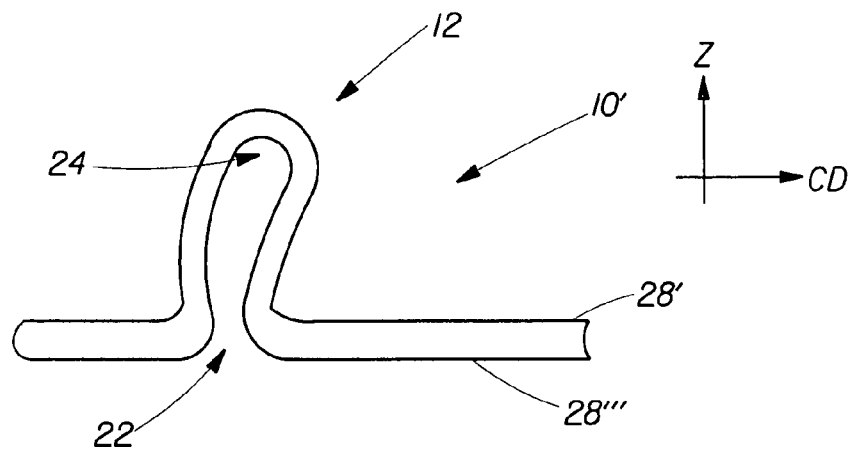
FIG. 11 is a schematic representation of a portion of a web structure of the present invention.
Figure 12:
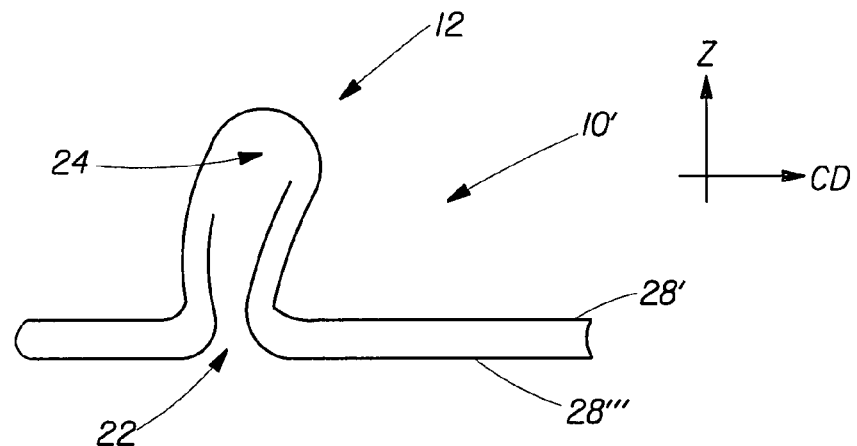
FIG. 12 is another schematic representation of a portion of a web structure of the present invention.
Figure 13:
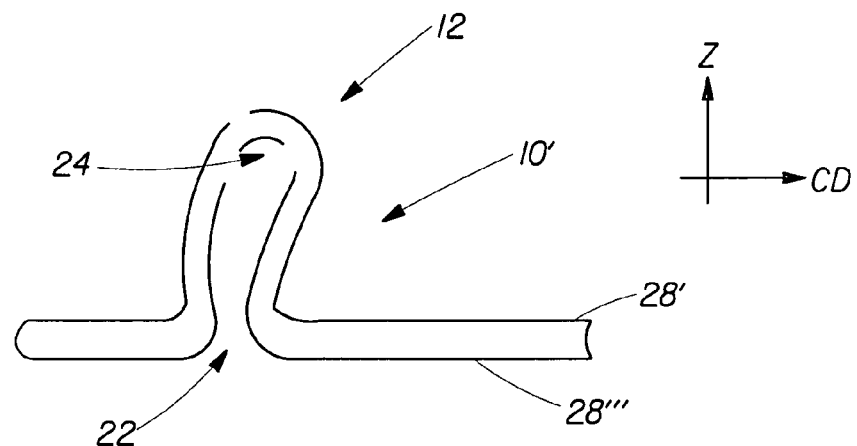
FIG. 13 is another schematic representation of a portion of a web structure of the present invention.

Multi-ply web structures can have significant advantages over single ply web structures. For example, a tuft from a multi-ply web structure using two or more precursor plies is shown schematically in FIGS. 11-15. As shown, both precursor plies 28' and 28" contribute fibers to tuft 12 in a "nested" relationship that "locks" the two precursor plies together, forming a laminate web structure without the use or need of adhesives or thermal bonding between the plies. However, if desired an adhesive, chemical bonding, resin or powder bonding, or thermal bonding between the plies can be selectively utilized to certain regions or all of the precursor plies. In addition, the multiple plies may be bonded during processing by any suitable bonding method by applying an adhesive or by thermal bonding without the addition of a separate adhesive. Also, bonding may be achieved by physically subjecting the two plies to the tuft generating process such that tufts, especially tufts from at least one ply protrude through the other ply. In a preferred example, the tuft 12 retains the ply relationship of the laminate precursor web, as shown in FIG. 11, and in all preferred examples the upper ply (specifically ply 28' in FIGS. 11-15, but in general the top ply with reference to the z-axis as shown in FIGS. 11-15) remains substantially intact and forms tufted fibers 26.

In a multi-ply web structure 10' each precursor ply can have different properties. For example, as shown in FIGS. 11-15, multi-ply web structures 10' can comprise two (or more) precursor webs, e.g., first and second precursor webs 28' and 28". First precursor web 28' can form an upper ply exhibiting high elongation and significant elastic recovery which enables the precursor web 28' to spring back. The spring back or lateral squeeze that results from precursor web 28' spring back aids in securing and stabilizing the z-axis oriented fibers in the tuft 12. The lateral squeeze provided by precursor web 28' can also increase the stability of the second precursor web 28".

Figure 14:
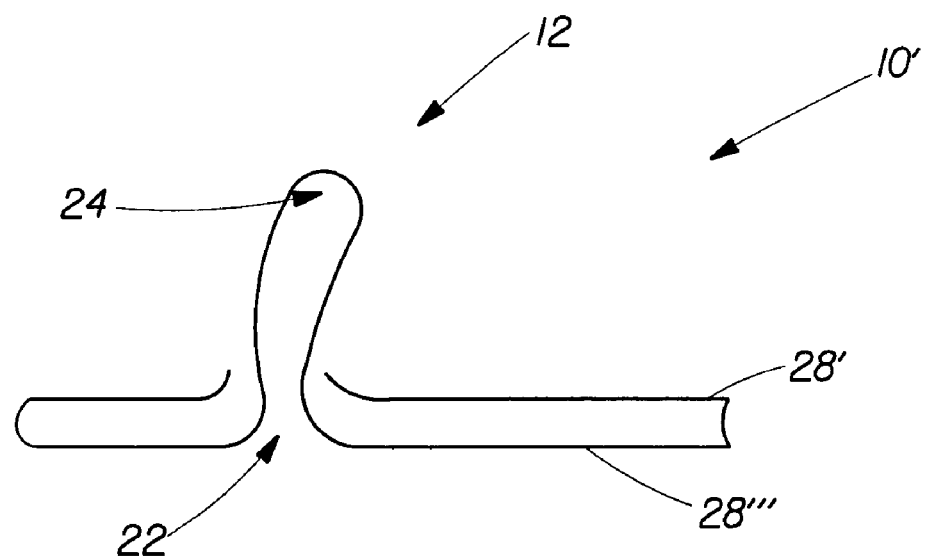
FIG. 14 is another schematic representation of a portion of a web structure of the present invention.

As shown in FIG. 14, the multi-ply web structure 10' of the present invention comprises a first precursor web 28' and a second precursor web 28". The second precursor web 28" forms a tuft 12 that protrudes through the first precursor web 28'.

Figure 15:
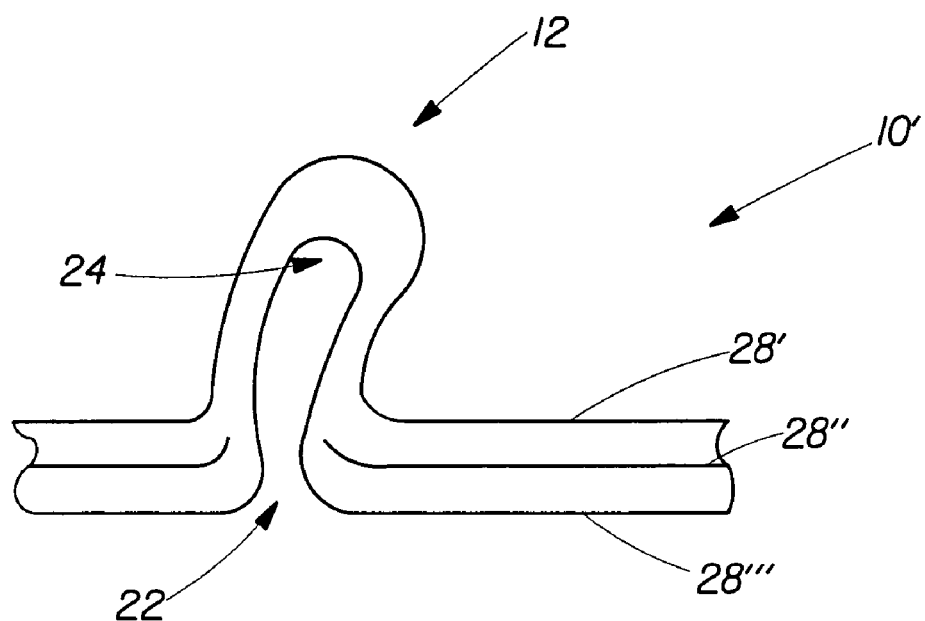
FIG. 15 is another schematic representation of a portion of a web structure of the present invention.

As shown in FIG. 15, the multi-ply web structure 10' of the present invention comprises a first precursor web 28', a second precursor web 28" and a third precursor web 28'''. The third precursor web 28''' forms a tuft 12 that protrudes through the second precursor web 28" and only into the first precursor web 28'.

In all of the multi-ply web structure examples illustrated in FIGS. 11-15, the formation of the tufts results in a discontinuity 22 and an open void area 24.

The web structures of the present invention, addition to being used as web products, may also be used for a wide variety of other applications. Nonlimiting examples of such other applications include various filter sheets such as air filter, bag filter, liquid filter, vacuum filter, water drain filter, and bacterial shielding filter; sheets for various electric appliances such as capacitor separator paper, and floppy disk packaging material; various industrial sheets such as tacky adhesive tape base cloth, oil absorbing material, and paper felt; various wiper sheets such as wipers for homes, services and medical treatment, printing roll wiper, wiper for cleaning copying machine, and wiper for optical systems; hygiene or personal cleansing wiper such as baby wipes, feminine wipes, facial wipes, or body wipes, various medicinal and sanitary sheets, such as surgical gown, gown, covering cloth, cap, mask, sheet, towel, gauze, base cloth for cataplasm, diaper, diaper core, diaper acquisition layer, diaper liner, diaper cover, base cloth for adhesive plaster, wet towel, and tissue; various sheets for clothes, such as padding cloth, pad, jumper liner, and disposable underwear; various life material sheets such as base cloth for artificial leather and synthetic leather, table top, wall paper, shoji-gami (paper for paper screen), blind, calendar, wrapping, and packages for drying agents, shopping bag, suit cover, and pillow cover; various agricultural sheets, such as cow carpets, cooling and sun light-shielding cloth, lining curtain, sheet for overall covering, light-shielding sheet and grass preventing sheet, wrapping materials of pesticides, underlining paper of pots for seeding growth; various protection sheets such as fume prevention mask and dust prevention mask, laboratory gown, and dust preventive clothes; various sheets for civil engineering building, such as house wrap, drain material, filtering medium, separation material, overlay, roofing, tuft and carpet base cloth, wall interior material, soundproof or vibration reducing sheet, and curing sheet; and various automobile interior sheets, such as floor mat and trunk mat, molded ceiling material, head rest, and lining cloth, in addition to a separator sheet in alkaline batteries.

Another advantage of the process described to produce the web structures of the present invention is that the web structures can be produced in-line with other web structure production equipment. Additionally, there may be other solid state formation processes that can be used either prior to or after the process of the present invention.

As can be understood from the above description of the web structures and methods for making such web structure of the present invention, many various web structures can be made without departing from the scope of the present invention as claimed in the appended claims. For example, web structures can be coated or treated with lotions, medicaments, cleaning fluids, anti-bacterial solutions, emulsions, fragrances, surfactants.

Test Methods

All tests described herein including those described under the Definitions section and the following test methods are conducted on samples that have been conditioned in a conditioned room at a temperature of 73° F. ±4° F. (about 23° C. ±2.2° C.) and a relative humidity of 50% ±10% for 24 hours prior to the test. Further, all tests are conducted in such conditioned room. Tested samples and felts should be subjected to 73° F. ±4° F. (about 23° C. ±2.2° C.) and a relative humidity of 50% ±10% for 24 hours prior to capturing images.

Fiber Diameter Test Method

A polymeric structure comprising fibers of appropriate basis weight (approximately 5 to 20 grams/square meter) is cut into a rectangular shape, approximately 20 mm by 35 mm. The sample is then coated using a SEM sputter coater (EMS Inc, PA, USA) with gold so as to make the fibers relatively opaque. Typical coating thickness is between 50 and 250 nm. The sample is then mounted between two standard microscope slides and compressed together using small binder clips. The sample is imaged using a 10× objective on an Olympus BHS microscope with the microscope light-collimating lens moved as far from the objective lens as possible. Images are captured using a Nikon D1 digital camera. A Glass microscope micrometer is used to calibrate the spatial distances of the images. The approximate resolution of the images is 1 μm/pixel. Images will typically show a distinct bimodal distribution in the intensity histogram corresponding to the fibers and the background. Camera adjustments or different basis weights are used to achieve an acceptable bimodal distribution. Typically 10 images per sample are taken and the image analysis results averaged.

The images are analyzed in a similar manner to that described by B. Pourdeyhimi, R. and R. Dent in "Measuring fiber diameter distribution in nonwovens" (Textile Res. J. 69(4) 233-236, 1999). Digital images are analyzed by computer using the MATLAB (Version. 6.3) and the MATLAB Image Processing Tool Box (Version 3.)The image is first converted into a grayscale. The image is then binarized into black and white pixels using a threshold value that minimizes the intraclass variance of the thresholded black and white pixels. Once the image has been binarized, the image is skeltonized to locate the center of each fiber in the image. The distance transform of the binarized image is also computed. The scalar product of the skeltonized image and the distance map provides an image whose pixel intensity is either zero or the radius of the fiber at that location. Pixels within one radius of the junction between two overlapping fibers are not counted if the distance they represent is smaller than the radius of the junction. The remaining pixels are then used to compute a length-weighted histogram of fiber diameters contained in the image.

Effective Caliper Test

Effective caliper of a fibrous structure and/or sanitary tissue product in roll form is determined by the following equation:

$$EC=(RD^2-CD^2)/(0.00127 \times SC \times SL)$$

wherein EC is effective caliper in mils of a single sheet in a wound roll of fibrous structure and/or sanitary tissue product; RD is roll diameter in inches; CD is core diameter in inches; SC is sheet count; and SL is sheet length in inches.

All documents cited in the Detailed Description of the Invention are, in relevant part, incorporated by reference herein; the citation of any document is not to be construed as an admission that it is prior art with respect to the present invention. To the extent that any meaning or definition of the term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary tissue product comprising a web structure comprising a tuft that defines an open void area tunnel, wherein the web structure comprises a first fiber comprising a crosslinked, hydroxyl polymer selected from the group consisting of starch, starch derivatives and mixtures thereof and wherein the tuft comprises the first fiber and wherein the web structure further comprises a second fiber having a chemically different composition relative to the first fiber comprising the crosslinked, hydroxyl polymer wherein the sanitary tissue product further comprises an additional ply of a web structure such that the tuft protrudes at least into the additional ply.

2. The sanitary tissue product according to claim 1 wherein the tuft protrudes through the additional ply.

3. The sanitary tissue product according to claim 1 wherein the polymeric structure further comprises a hydroxyl polymer selected from the group consisting of: polyvinyl alcohol, polyvinyl alcohol derivatives, chitosan, chitosan derivatives, cellulose derivatives, gums, arabinans, galactans, proteins, and mixtures thereof.

4. The sanitary tissue product according to claim 1 wherein the web structure comprises a plurality of tufts.

5. The sanitary tissue product according to claim 4 wherein the plurality of tufts are uniformly distributed on the web structure.

6. The sanitary tissue product according to claim 1 wherein the web structure comprises a plurality of substantially randomly oriented first fibers.

7. The sanitary tissue product according to claim 1 wherein the first fiber has a fiber diameter of less than about 50 μm.

8. The sanitary tissue product according to claim 1 wherein at least a portion of the first fiber exhibits no melting point.

9. The sanitary tissue product according to claim 1 wherein the tuft is integral with, but extends from the web structure.

10. A sanitary tissue product comprising a layered web structure comprising a first layer and a second layer, wherein the first layer comprises a first composition and the second layer comprises a second composition, wherein the first and second compositions are chemically different such that the first layer exhibits an extensibility different from the second layer, wherein a portion of one layer protrudes at least into the other layer such that a surface of the layered web structure comprises a tuft that defines an open void area tunnel, wherein the layered web structure comprises a polymeric structure comprising a crosslinked, hydroxyl polymer selected from the group consisting of starch, starch derivatives and mixtures thereof and wherein the tuft comprises the crosslinked, hydroxyl polymer.

11. The sanitary tissue product according to claim 10 wherein the first composition comprises the polymeric structure.

12. The sanitary tissue product according to claim 10 wherein the polymeric structure further comprises a hydroxyl polymer selected from the group consisting of: polyvinyl alcohol, polyvinyl alcohol derivatives, chitosan, chitosan derivatives, cellulose derivatives, gums, arabinans, galactans, proteins, and mixtures thereof.

13. The sanitary tissue product according to claim 10 wherein the layered web structure comprises a plurality of tufts.

14. The sanitary tissue product according to claim 13 wherein the plurality of tufts are uniformly distributed on the layered web structure.

15. The sanitary tissue product according to claim 10 wherein the layered web structure comprises a nonwoven web comprising substantially randomly oriented fibers.

16. The sanitary tissue product according to claim 10 wherein the fiber has a fiber diameter of less than about 50 μm.

17. The sanitary tissue product according to claim 10 wherein at least a portion of the fiber exhibits no melting point.

18. The sanitary tissue product according to claim 10 wherein the polymeric structure is in the form of a film.

19. The sanitary tissue product according to claim 10 wherein the tuft is integral with, but extends from the layered web structure.

20. The sanitary tissue product according to claim 10 wherein the sanitary tissue product further comprises an additional ply of a web structure such that the tuft protrudes at least into the additional ply.

21. The sanitary tissue product according to claim 20 wherein the tuft protrudes through the additional ply.

* * * * *